(12) United States Patent
Yeo et al.

(10) Patent No.: US 7,618,347 B2
(45) Date of Patent: Nov. 17, 2009

(54) TRAINING CONTROL METHOD AND APPARATUS USING BIOFEEDBACK

(75) Inventors: Hyung-sok Yeo, Suwon-si (KR); Jae-chan Park, Daejeon-si (KR); Kun-soo Shin, Seongnam-si (KR); Kyung-ho Kim, Yongin-si (KR); Jeong-hwan Lee, Suwon-si (KR); Youn-ho Kim, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 845 days.

(21) Appl. No.: 10/934,764

(22) Filed: Sep. 7, 2004

(65) Prior Publication Data

US 2005/0124463 A1 Jun. 9, 2005

(30) Foreign Application Priority Data

Sep. 4, 2003 (KR) .................... 10-2003-0061944

(51) Int. Cl.
*A63B 71/00* (2006.01)
(52) U.S. Cl. .................................. 482/8; 482/1; 482/9
(58) Field of Classification Search ................ 482/1–9, 482/900–902; 434/236, 247; 709/218
See application file for complete search history.

(56) References Cited

U.S. PATENT DOCUMENTS

| | | | |
|---|---|---|---|
| 4,776,323 A | 10/1988 | Spector | |
| 5,215,468 A * | 6/1993 | Lauffer et al. | 434/236 |
| 5,319,355 A | 6/1994 | Russek | |
| 5,577,510 A | 11/1996 | Chittum et al. | |
| 5,740,812 A | 4/1998 | Cowan | |
| 5,941,837 A | 8/1999 | Amano et al. | |
| 5,993,401 A | 11/1999 | Inbe et al. | |
| 6,026,335 A | 2/2000 | Atlas | |
| 6,027,428 A * | 2/2000 | Thomas et al. | 482/4 |
| 6,345,197 B1 | 2/2002 | Fabrizio | |
| 6,443,614 B1 | 9/2002 | Read | |
| 6,447,424 B1 * | 9/2002 | Ashby et al. | 482/8 |
| 6,554,776 B1 | 4/2003 | Snow et al. | |
| 6,572,511 B1 * | 6/2003 | Volpe | 482/4 |
| 6,634,992 B1 * | 10/2003 | Ogawa | 482/8 |
| 6,702,719 B1 * | 3/2004 | Brown et al. | 482/8 |
| 6,716,139 B1 | 4/2004 | Hosseinzadehdolkhani | |
| 6,808,473 B2 * | 10/2004 | Hisano et al. | 482/8 |

(Continued)

FOREIGN PATENT DOCUMENTS

DE 42 28 091 3/1994

(Continued)

OTHER PUBLICATIONS

Itami, et al. *, Tranactions of the Information Processing Society of Japan, 44(2):478-485 (Feb. 2003) *Entitled: Virtual aerobics system with accurate motion speed control.

(Continued)

*Primary Examiner*—Glenn Richman
(74) *Attorney, Agent, or Firm*—Cantor Colburn LLP (57) ABSTRACT

In a training control method using biofeedback, and an apparatus using the method, the method includes setting a target exercise zone for a user based on a bio-signal from the user, the target exercise zone including a range of indices and comparing a current index obtained from the bio-signal with the target exercise zone in time units in an exercise training mode and providing at least one of positive biofeedback information, negative biofeedback information, and a warning message to the user according to a result of the comparison.

15 Claims, 7 Drawing Sheets

U.S. PATENT DOCUMENTS

2002/0091796 A1* 7/2002 Higginson et al. .......... 709/218

FOREIGN PATENT DOCUMENTS

| DE | 199 55 720 | 5/2001 |
| --- | --- | --- |
| EP | 1 128 358 A1 | 8/2001 |
| JP | 06-502270 | 3/1994 |
| JP | 09-238911 | 9/1997 |
| JP | 2000-070373 | 3/2000 |
| JP | 2001-299980 | 10/2001 |
| JP | 2002-153430 | 5/2002 |
| JP | 2002-330933 | 11/2002 |
| JP | 2002-346013 | 12/2002 |
| JP | 2003-164430 | 6/2003 |
| KR | 1998-7002477 | 7/1998 |
| KR | 1999-0063100 | 7/1999 |
| KR | 2000-0064072 | 11/2000 |
| KR | 2002-0011730 | 2/2002 |
| KR | 2002-0015907 | 3/2002 |
| KR | 2002-0083004 | 11/2002 |
| WO | WO 93/01574 | 1/1993 |
| WO | WO 97/14357 | 4/1997 |

OTHER PUBLICATIONS

Nicolae, et al. , International Symposium on Biotelemetry, pp. 173-175 (1972) Entitled: "'Cardiocomandor' an electronic portable schedule apparatus used by top athletes for conducting self interval training".

* cited by examiner

TRAINING CONTROL METHOD AND APPARATUS USING BIOFEEDBACK

BACKGROUND OF THE INVENTION

1. Field of the Invention

The present invention relates to a training control method and apparatus. More particularly, the present invention relates to a method and apparatus for controlling exercise training and rest stability training using biofeedback.

2. Description of the Related Art

Biofeedback is a technique of providing information on a change in a physiological state of a user's body in real time based on various bio-signals collected from the body and providing an appropriate signal to the user when the change in the physiological state reaches a target value, thereby allowing the user to learn to practice self-control over the particular physiological state, e.g., heart rate or respiration rate.

Heart rate (HR) is a cardiovascular index that is most prominently observed when people alternate between exercise and rest. The HR can be collected using various methods. Usually, the HR is measured by counting the number of pulses per unit time using an electrocardiogram signal or a photo plethysmography (PPG) signal. The HR is the number of heart beats per minute and is expressed in beats per minute (BPM). An HR of a normal adult is about 60-90 BPM. A person's HR increases when the person exercises, becomes excited, or runs a fever. A person's HR decreases when the person is at rest, is mentally stable or relaxed, or is asleep.

Based on these characteristics, sports medicine applies various training techniques to teach effective self-control using a biofeedback technique in which a user's HR is measured and reported to the user and an appropriate signal is provided to the user when the user's HR reaches a predetermined target value.

It is known that positive effects of aerobic exercises, such as walking, jogging, cycling, and swimming, which develop endurance, can be obtained when each aerobic exercise is continuously performed and controlled in its intensity such that a specific target HR is maintained. A target HR can be easily obtained using a Karvonen formula to calculate a minimum target HR and a maximum target HR. Usually, in sports medicine, a proper exercise zone is determined by setting the minimum target HR as a lower limit and the maximum target HR as an upper limit. A person is then instructed to exercise continuously for a predetermined period of time such that an HR measured during the exercise remains within the proper exercise zone in order to maximize an effect of the exercise.

As described above, there are various conventional techniques for measuring an amount of exercise or for motivating a user to exercise. In conventional techniques, usually, a maximum target HR and a minimum target HR are defined referring to a user's HR, and the user is allowed to recognize a current exercise level through a display device or an alarm function so that the user can continue the exercise within a predetermined level range based on the maximum target HR and the minimum target HR.

There are several considerations regarding how a user checks his/her bio-information while exercising. Firstly, the user's freedom of movement should be maximized while exercising. Secondly, a procedure for recognizing a continuous change in bio-information should not disturb the user during the exercise. Thirdly, when biofeedback information is provided to the user to motivate him/her to continue exercising, a signal stimulating enough to motivate the user to continue the exercise should be effectively presented to the user. These considerations similarly apply when a user checks his/her bio-information while resting.

According to conventional techniques, however, an HR measuring module is not convenient and restricts a user's freedom of movement. In addition, it is not easy for the user to recognize a change in bio-information during exercise, which may interrupt the user's continuous exercise. For example, in many conventional sports medicine applications and cases using a sensor of a wireless HR monitor, the sensor is attached to the user's chest. In order to collect reliable signals, a band is tightened around the user's body to place the sensor in close contact with the chest.

SUMMARY OF THE INVENTION

The present invention is therefore directed to a method and apparatus for controlling exercise training and rest stability training using biofeedback, which substantially overcome one or more of the problems due to the limitations and disadvantages of the related art.

It is a feature of an embodiment of the present invention to provide a method and apparatus by which a bio-signal is collected from a body of a user while exercising and is analyzed in real time, and a result of the analysis and biofeedback information corresponding to a change in a level of the bio-signal are provided to the user, thereby allowing the user to recognize this change from the biofeedback information during the exercise and train to adjust an intensity of the exercise according to the change.

It is another feature of an embodiment of the present invention to provide a method and apparatus by which a bio-signal is collected from a body of a user while resting and is analyzed in real time, and a result of the analysis and biofeedback information corresponding to a change level of the bio-signal are provided to the user, thereby allowing the user to recognize this change from the biofeedback information during the rest and train to effectively reach a stable resting state.

It is still another feature of an embodiment of the present invention to provide a method and apparatus by which a bio-signal is collected from a body of a user resting or exercising and is analyzed in real time, a result of the analysis is stored in a separate data memory device, thereby facilitating continuous management of general items of health information related to the user's exercise and rest, which can be used to promote the user's health.

It is yet another feature of an embodiment of the present invention to provide a method and apparatus for minimizing restriction of movement in a method and apparatus for collecting a bio-signal from a body of a user resting or exercising and analyzing the bio-signal in real time, thereby effectively providing comfort and convenience to the user.

At least one of the above features and other advantages may be provided by an exercise training control method using biofeedback including setting a target exercise zone for a user based on a bio-signal from the user, the target exercise zone including a range of indices and comparing a current index obtained from the bio-signal with the target exercise zone in time units in an exercise training mode and providing at least one of positive biofeedback information, negative biofeedback information, and a warning message to the user according to a result of the comparison.

Setting the target exercise zone for the user based on the bio-signal from the user may include calculating a maximum target heart rate using an initial heart rate of the user and user information and using the maximum target heart rate to set the target exercise zone.

Comparing the current index obtained from the bio-signal with the target exercise zone in time units in the exercise training mode and providing at least one of positive biofeedback information, negative biofeedback information, and the warning message to the user according to the result of the comparison may include comparing a current heart rate of the user with the target exercise zone, providing the positive biofeedback information to the user, when it is determined as a result of the comparison that the current heart rate remains within the target exercise zone for longer than a first time, providing the negative biofeedback information to the user, when it is determined as the result of the comparison that the current heart rate remains below the target exercise zone for longer than a second time, and providing the warning message to the user, when it is determined as the result of the comparison that the current heart rate is greater than the target exercise zone.

The positive biofeedback information may include a plurality of music files having a beat similar to an average heart rate in the target exercise zone, and the negative biofeedback information may include a plurality of music files having a beat similar to the lower limit of the target exercise zone through a beat similar to the average heart rate in the target exercise zone.

Comparing the current index obtained from the bio-signal with the target exercise zone in time units in the exercise training mode and providing at least one of positive biofeedback information, negative biofeedback information, and the warning message to the user according to a result of the comparison may include comparing a current heart rate of the user with the target exercise zone, providing the positive biofeedback information to the user, when it is determined as a result of the comparison that the current heart rate remains below the target exercise zone for longer than a first time in an initial stage of exercise, providing the negative biofeedback information to the user, when it is determined as the result of the comparison that the current heart rate has decreased below the target exercise zone for longer than a second time after remaining within the target exercise zone during the exercise, and providing the warning message to the user, when it is determined as the result of the comparison that the current heart rate is greater than the target exercise zone.

The positive biofeedback information may include a plurality of music files having a beat similar to the lower limit of the target exercise zone through a beat similar to the average heart rate in the target exercise zone, and the negative biofeedback information may include a plurality of music files having a slower beat than the current heart rate.

At least one of the above features and other advantages may be provided by a rest training control method using biofeedback including setting a target resting zone for a user based on a bio-signal from the user, the resting target zone including a range of indices and comparing a current index obtained from the bio-signal with the target resting zone in time units in a rest training mode and providing at least one of positive biofeedback information and negative biofeedback information to the user according to a result of the comparison.

Setting a target resting zone for a user based on a bio-signal from the user may include calculating a minimum target heart rate using an initial heart rate of the user and user information and using the minimum target heart rate to set the target resting zone.

Comparing the current index obtained from the bio-signal with the target resting zone in time units in the rest training mode and providing at least one of positive biofeedback information and negative biofeedback information to the user according to the result of the comparison may include comparing a current heart rate of the user with the target resting zone, providing the positive biofeedback information to the user, when it is determined as a result of the comparison that the current heart rate remains within the target resting zone for longer than a first time, providing the negative biofeedback information to the user, when it is determined as the result of the comparison that the current heart rate remains above the target resting zone for longer than a second time, and stopping biofeedback, when it is determined as the result of the comparison that the current heart rate remains within the target resting zone for longer than a third time or less than the target resting zone.

The positive biofeedback information may include a plurality of music files having a beat similar to an average heart rate in the target resting zone, and the negative biofeedback information may include a plurality of music files having a beat similar to the upper limit of the target resting zone through a beat similar to the average heart rate in the target resting zone.

Comparing the current index obtained from the bio-signal with the target resting zone in time units in the rest training mode and providing at least one of positive biofeedback information and negative biofeedback information to the user according to the result of the comparison may include comparing a current heart rate of the user with the target resting zone, providing the positive biofeedback information to the user, when it is determined as a result of the comparison that the current heart rate remains above the target resting zone for longer than a first predetermined time in an initial stage of resting, providing the negative biofeedback information to the user, when it is determined as the result of the comparison that the current heart rate is above the target resting zone for longer than a second predetermined time after remaining within the target resting zone during the resting, and stopping biofeedback, when it is determined as the result of the comparison that the current heart rate remains within the target resting zone for longer than a third time or is less than the target resting zone.

The positive biofeedback information may include a plurality of music files having a beat similar to the upper limit of the target resting zone through a beat similar to an average heart rate in the target resting zone, and the negative biofeedback information may include a plurality of music files having a faster beat than the current heart rate.

At least one of the above features and other advantages may be provided by a training control method using biofeedback including setting a target resting zone and a target exercise zone for a user based on a bio-signal from the user, the target resting zone and the target exercise zone including a first and a second range of indices, respectively, selecting one of an exercise training mode and a rest training mode, comparing an index obtained from the bio-signal with the target exercise zone in time units in the exercise training mode and providing at least one of a first positive biofeedback information, a first negative biofeedback information, and a warning message to the user according to a result of the comparison, and comparing the index obtained from the bio-signal with the target resting zone in time units in the rest training mode and providing at least one of a second positive biofeedback information and a second negative biofeedback information to the user according to a result of the comparison.

Setting a target resting zone and a target exercise zone for a user based on a bio-signal from the user may include calculating a minimum target heart rate and a maximum target heart rate using an initial heart rate of the user and user information and using the minimum target heart rate to set the target resting zone and using the maximum target heart rate to set the target exercise zone.

Comparing the index obtained from the bio-signal with the target exercise zone in time units in the exercise training mode and providing at least one of the first positive biofeedback information, the first negative biofeedback information, and the warning message to the user according to a result of the comparison may include comparing a current heart rate of the user with the target exercise zone, providing the first positive biofeedback information to the user to maintain the current heart rate within the target exercise zone, when it is determined as a result of the comparison that the current heart rate remains within the target exercise zone for longer than a first time, providing the first negative biofeedback information to the user to increase the current heart rate to the target exercise zone, when it is determined as the result of the comparison that the current heart rate remains below the target exercise zone for longer than a second time, and providing the warning message to the user, when it is determined as the result of the comparison that the current heart rate is greater than the target exercise zone.

The first positive biofeedback information may include a plurality of music files having an identical beat, and the first negative biofeedback information may include a plurality of music files having different beats.

Comparing the index obtained from the bio-signal with the target resting zone in time units in the rest training mode and providing at least one of the second positive biofeedback information and the second negative biofeedback information to the user according to the result of the comparison may include comparing a current heart rate of the user with the target resting zone, providing the second positive biofeedback information to the user, when it is determined as a result of the comparison that the current heart rate remains within the target resting zone for longer than a first time, providing the second negative biofeedback information to the user, when it is determined as the result of the comparison that the current heart rate remains above the target resting zone for longer than a second time, and stopping biofeedback, when it is determined as the result of the comparison that the current heart rate remains within the target resting zone for longer than a third time or is less than the target resting zone.

The second positive biofeedback information may include a plurality of music files having an identical beat, and the second negative biofeedback information may include a plurality of music files each of different beats.

At least one of the above features and other advantages may be provided by a training control apparatus using biofeedback including a bio-signal measuring module for measuring a bio-signal from a user and for providing predetermined biofeedback information to the user, and a bio-information feedback module for setting a target exercise zone and a target resting zone using the bio-signal received from the bio-signal measuring module and user information, for comparing the bio-signal with a target zone, and for providing at least one of positive biofeedback information and negative biofeedback information to the bio-signal measuring module according to a result of the comparison.

The bio-information feedback module may include a memory for storing a plurality of music files having different beats.

The bio-information feedback module may provide a plurality of music files having an identical beat or a plurality of music files having different beats to the user as the positive or negative biofeedback information according to a current heart rate obtained from the bio-signal in an exercise training mode to lead the current heart rate to the target exercise zone or to inform the user of a deviation from the target exercise zone.

The bio-information feedback module may provide a plurality of music files having an identical beat or a plurality of music files having different beats to the user as the positive or negative biofeedback information according to a current heart rate obtained from the bio-signal in an resting training mode to lead the current heart rate to the target resting zone or to inform the user of a deviation from the target resting zone.

At least one of the above features and other advantages may be provided by a health managing system using biofeedback information including a bio-signal measuring module for measuring a bio-signal from a user and for providing predetermined biofeedback information to the user, a bio-information feedback module for setting a target exercise zone and a target resting zone using the bio-signal received from the bio-signal measuring module and user information, for comparing the bio-signal with either of the target exercise zone or the target resting zone according to a preselected training mode, and for providing at least one of positive biofeedback information, negative biofeedback information, and a warning message in the selected training mode to the bio-signal measuring module according to a result of the comparison, and a health information management server for receiving the bio-signal and bio-information from the bio-information feedback module, for periodically managing a result of analyzing the bio-signal and the bio-information as health information of the user, and for transmitting the periodic health information to the bio-information feedback module so that the periodic health information is provided to the user.

The health information management server may be installed at either of a data center and a base station. The health information may be transmitted from the health information management server to the bio-information feedback module in a form of one among a voice message, a text message, and e-mail.

In either of the embodiments, the bio-signal measuring module may be a headset including a speaker, a transmissive light sensor, and a wireless transceiver. The bio-information feedback module may be one selected from the group consisting of a mobile communication terminal, a personal digital assistant (PDA) capable of wireless data communication, and a wristwatch-type information terminal.

The training control methods may be implemented by a program recorded in a computer-readable recording medium.

In any of the above embodiments, the index may be a heart rate of the user.

BRIEF DESCRIPTION OF THE DRAWINGS

The above and other features and advantages of the present invention will become more apparent to those of ordinary skill in the art by describing in detail exemplary embodiments thereof with reference to the attached drawings in which.

DETAILED DESCRIPTION OF THE INVENTION

Korean Patent Application No. 2003-61944, filed on Sep. 4, 2003, in the Korean Intellectual Property Office, and entitled: "Training Control Method and Apparatus Using Biofeedback," is incorporated by reference herein in its entirety.

The present invention will now be described more fully hereinafter with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art.

A training control method and apparatus according to an embodiment of the present invention are provided to allow a user exercising or resting to effectively reach a target exercise zone or a target resting zone through self-control using biofeedback. Accordingly, the training control apparatus that the user wears while resting or exercising needs to provide maximum comfort and convenience to the user. Further, a biofeedback algorithm for leading the user to the target exercise zone or the target resting zone needs to be effectively implemented.

Figure 1:
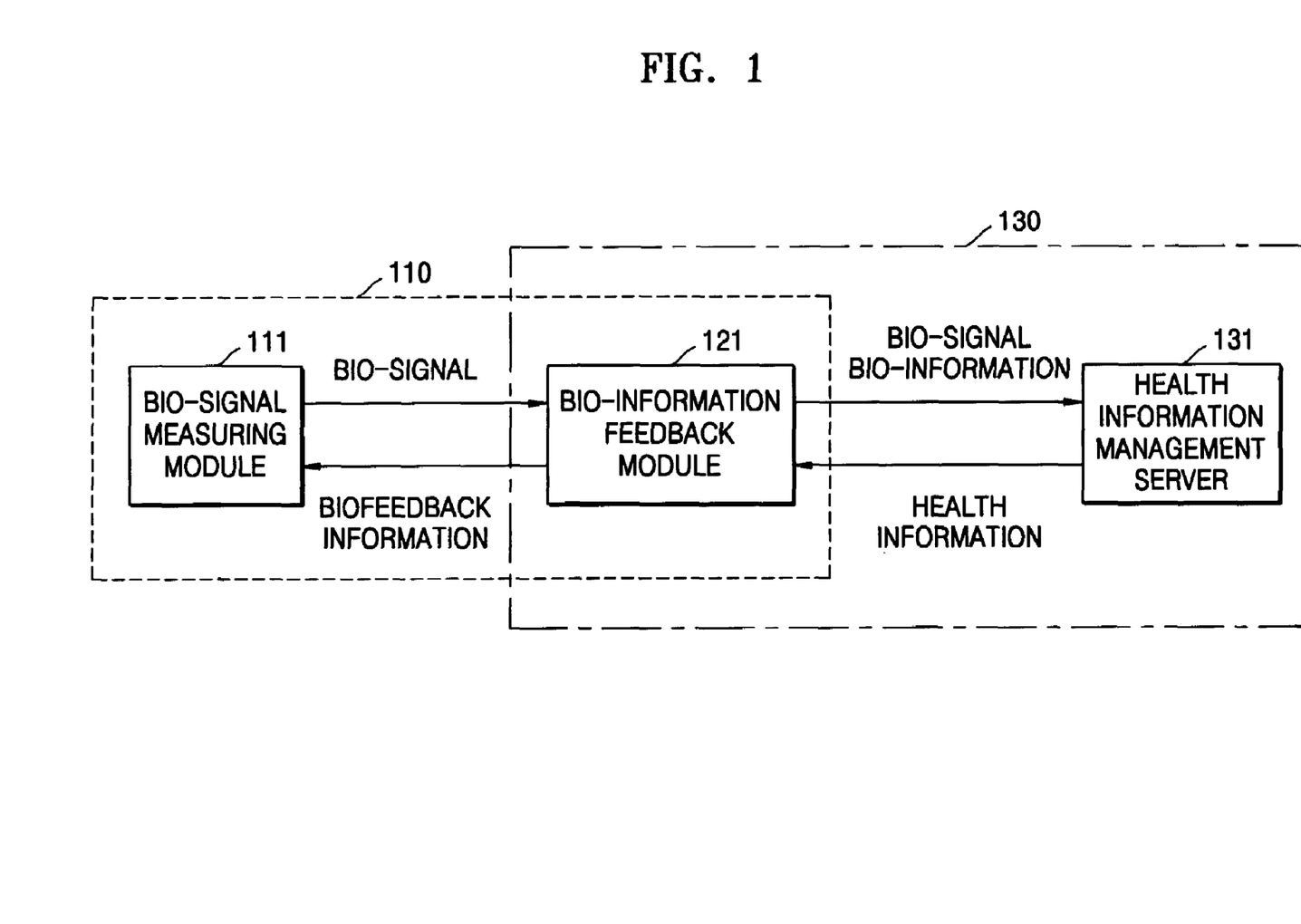
FIG. 1 is a block diagram of a training control apparatus according to an embodiment of the present invention.

FIG. 1 is a block diagram of a training control apparatus using biofeedback according to an embodiment of the present invention. The training control apparatus includes a biofeedback unit 110 including a bio-signal measuring module 111 and a bio-information feedback module 121. Additionally, the training control apparatus includes a health information management unit 130 including the bio-information feedback module 121 and a health information management server 131.

Referring to FIG. 1, the biofeedback unit 110 trains a user to learn self-control over a physiological condition, such as heart rate, using biofeedback so that the user can effectively exercise and rest. In the biofeedback unit 110, the bio-signal measuring module 111 may be implemented by a headset including a speaker, a photo plethysmography (PPG) sensor for counting a heart rate (HR), and a wireless transceiver so that both measurement and feedback can be performed. The bio-information feedback module 121 counts the user's HR based on a bio-signal, i.e., a PPG signal, which is wirelessly transmitted from the bio-signal measuring module 111, drives a predetermined feedback algorithm shown in FIG. 2 based on the HR, and wirelessly transmits biofeedback information to the bio-signal measuring module 111. The bio-information feedback module 121 may be implemented by a mobile communication terminal (e.g., a cellular phone), a personal digital assistant (PDA) capable of wireless data communication, or a wristwatch-type information terminal. Data communication between the bio-signal measuring module 111 and the bio-information feedback module 121 may be performed using local wireless communication, such as spread spectrum, ZigBee™, or a wireless personal area network (WPAN), or any other similar method.

The health information management unit 130 receives a user's bio-signal, continuously manages a user's bio-information based on the user's bio-signal and provides biofeedback information according to the user's bio-signal and bio-information to the bio-signal measuring module 111. In the health information management unit 130, the health information management server 131 may be installed at a data center or a base station. The health information management server 131 wirelessly receives the bio-signal and the bio-information from the bio-information feedback module 121, analyzes and manages health information periodically, e.g., daily, weekly, or monthly, and transmits the health information to the bio-information feedback module 121 in response to the user's request or at some predetermined interval. In the health information, a change in the bio-information is collected during the predetermined period, diagrammatized, and managed, thereby allowing the user to easily observe the periodical change in his/her bio-information and design a statistical exercise program suitable to the user according to the change. In addition, in the health information, relation between personal information including the user's age, sex, and height and the user's bio-information including weight, HR, respiratory rate, and body temperature per measurement is managed to be used as a fundamental database for clinical study and other health management service. The health information may be transmitted from the health information management server 131 to the bio-information feedback module 121 in the form of a voice message, a text message, e-mail, or any other form of communication.

Figure 2:
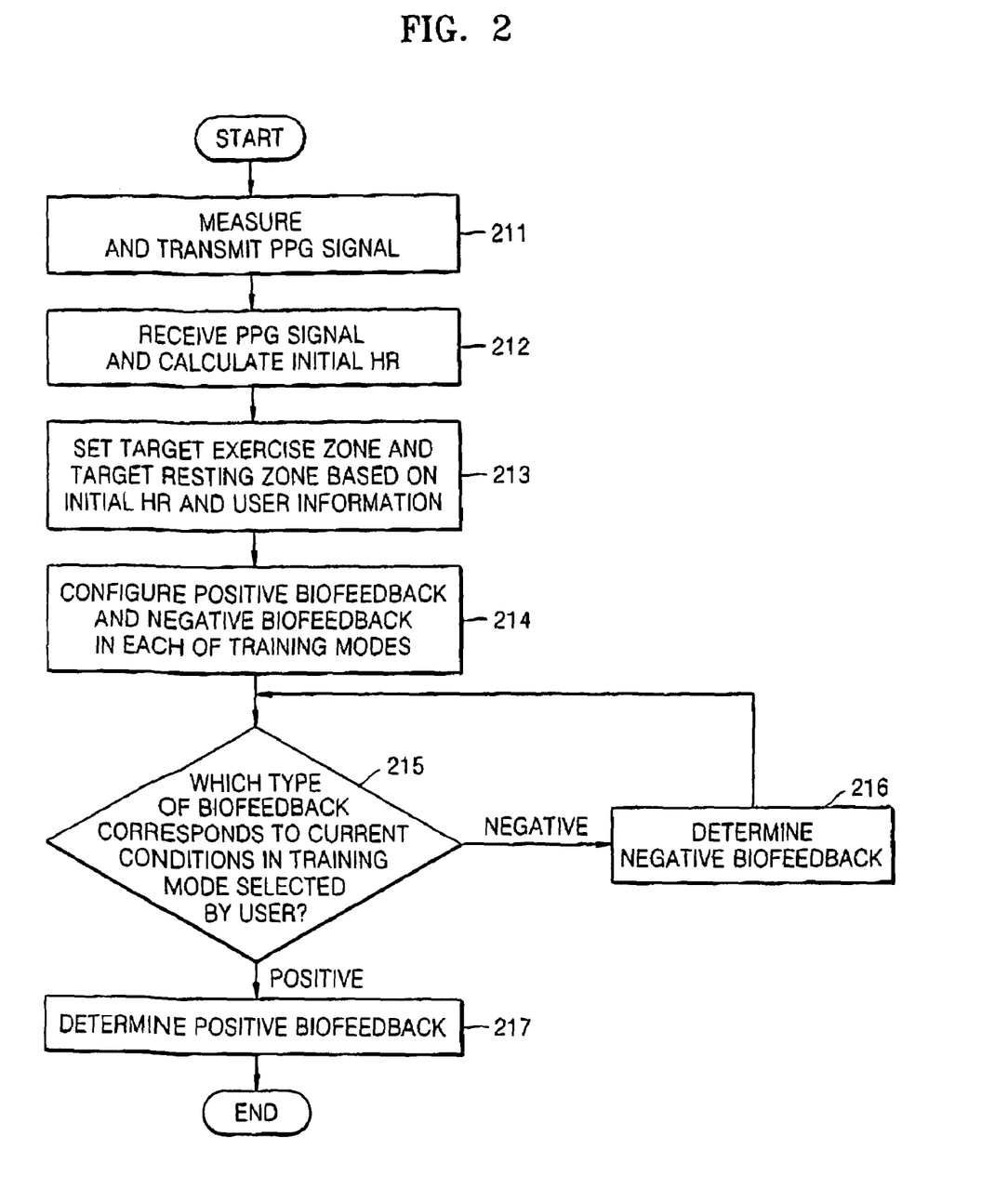
FIG. 2 is a flowchart of a training control method according to an embodiment of the present invention.

FIG. 2 is a flowchart of a training control method using biofeedback according to an embodiment of the present invention. The training control method includes measuring an HR, determining a maximum target HR and a minimum target HR, setting a target exercise zone and a target resting zone, and determining a first positive biofeedback and a first negative biofeedback in an exercise training mode or determining a second positive biofeedback and a second negative biofeedback in a rest training mode according to a user's selection of the exercise training mode or the rest training mode.

Referring to FIG. 2, in operation 211, a user's bio-signal, e.g., a PPG signal, is measured using the bio-signal measuring module 111 and is wirelessly transmitted to the bio-information feedback module 121.

In operation 212, pulses of the PPG signal wirelessly transmitted from the bio-signal measuring module 111 are counted and converted into an HR, and an initial HR is calculated. The initial HR is an average HR measured for, e.g., the first 30 seconds while the user is standing and putting on the bio-signal measuring module 111 without exercising. Meanwhile, the user's age data may be manually input to the bio-information feedback module 121 while the initial HR is measured, either before or after the user puts on the bio-signal measuring module 111.

In operation 213, a target exercise zone and a target resting zone are set based on user information corresponding to the user's age and the initial HR. For this operation, a maximum target HR and a minimum target HR are determined first. For example, according to the Karvonen formula, it may be defined that Minimum target HR=(220−Age−Initial HR)*0.6+Initial HR and Maximum target HR=(220−Age−Initial HR)*0.75+Initial HR.

Thereafter, the target exercise zone and the target resting zone are set based on the maximum target HR and the minimum target HR. The target exercise zone indicates an exercise zone in which the user can realize healthful benefits from exercise. Usually, when a normal adult continuously performs an exercise program for about 20 to 30 minutes within the target exercise zone, it is widely known that the user's ability to exercise improves and maximum benefits are realized. In an embodiment of the present invention, the target exercise zone is set to 90% of Maximum target HR±10% and the target resting zone is set to 80% of Minimum target HR±10%.

Since the target exercise zone and the target resting zone may be different depending on different users' physical conditions, a user may adjust the target exercise zone and the target resting zone to his/her own physical conditions when they are set. In other words, the user is able to adjust an upper limit and a lower limit of the target exercise zone based on the maximum target HR to be suitable to his/her physical conditions. The user is also able to adjust an upper limit and a lower limit of the target resting zone based on the minimum target HR to be suitable to his/her physical conditions.

In operation 214, application conditions, major functions, and feedback information with respect to a positive biofeedback and a negative biofeedback are set based on the target exercise zone and the target resting zone. This operation will be described in greater detail with reference to FIGS. 3 and 4.

Figure 3:
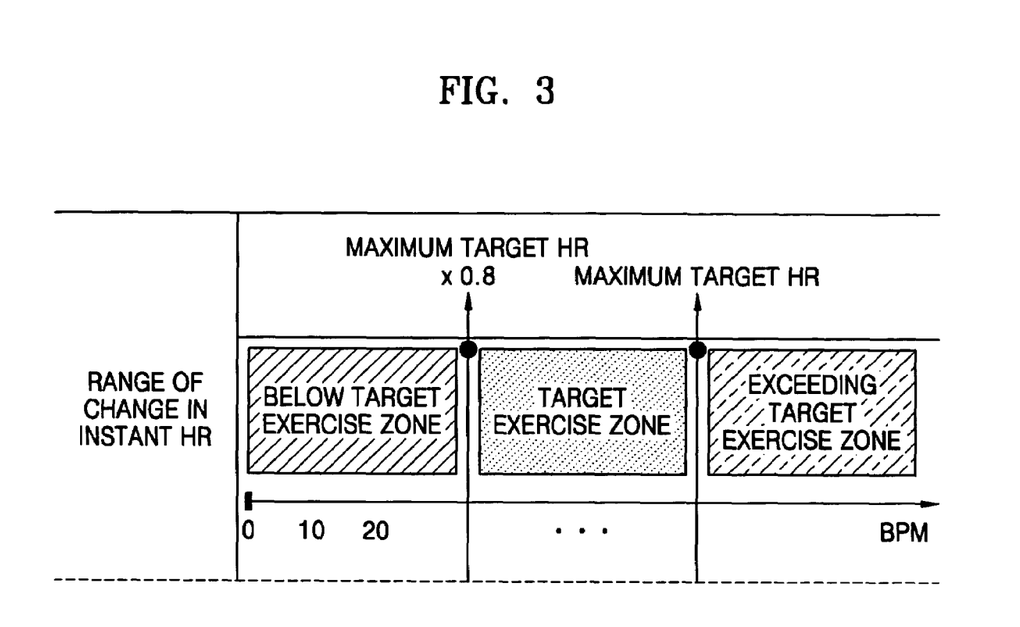
FIG. 3 illustrates a target exercise zone and its corresponding biofeedback.

Referring to FIG. 3, a zone below the lower limit of the target exercise zone, i.e., below 80% of the maximum target HR, is referred to as a "below target exercise zone." A zone exceeding the upper limit of the target exercise zone, i.e., exceeding 100% of the maximum target HR, is referred to as an "exceeding target exercise zone." In the exercise training mode, the first positive biofeedback and the first negative biofeedback may be determined based on the target exercise zone in one of the following two manners.

In the first manner, the first positive biofeedback is used when a current HR with a slight deviation continuously remains within the target exercise zone for a predetermined period of time and motivates the user to continue to perform the exercise to maintain his/her current HR within the target exercise zone. To implement the first positive biofeedback, the user hears several music files having rhythm similar to an average HR in the target exercise zone. The first negative biofeedback is used when the current HR with a slight deviation continuously remains within the below target exercise zone for a predetermined period of time and motivates the user to perform the exercise more vigorously to spontaneously raise the user's current HR to the target exercise zone. To implement the first negative biofeedback, the user hears several music files having rhythms gradually progressing from a beat similar to an HR corresponding to the lower limit of the target exercise zone to a faster beat similar to an average HR in the target exercise zone. In addition, when the current HR with a slight deviation continuously remains in the exceeding target exercise zone for a predetermined period of time, a voice message warning of the dangerous condition is provided to the user to stop him/her from exercising.

In the second manner, the first positive biofeedback is used when a current HR with a slight deviation continuously remains within the below target exercise zone for a predetermined period of time in an initial stage of exercise and motivates the user to perform the exercise more vigorously to spontaneously raise the current HR to the target exercise zone. To implement the first positive biofeedback, the user hears several music files having rhythms gradually progressing from a beat similar to an HR corresponding to the lower limit of the target exercise zone to a faster beat similar to an average HR in the target exercise zone. The first negative biofeedback is used when the current HR drops from the target exercise zone to the below target exercise zone during the exercise and thereafter. More specifically, when the current HR with a slight deviation continuously remains within the below target exercise zone for a predetermined period of time, after having been in the target exercise zone for a period of time, the first negative biofeedback is used to inform the user of a low intensity of the exercise. To implement the first negative biofeedback, the user hears several music files having rhythm of a slower beat than an average current HR for the predetermined period of time. In addition, when the current HR with a slight deviation continuously remains in the exceeding target exercise zone for a predetermined period of time, a voice message warning danger is provided to the user to stop him/her from exercising.

Figure 4:
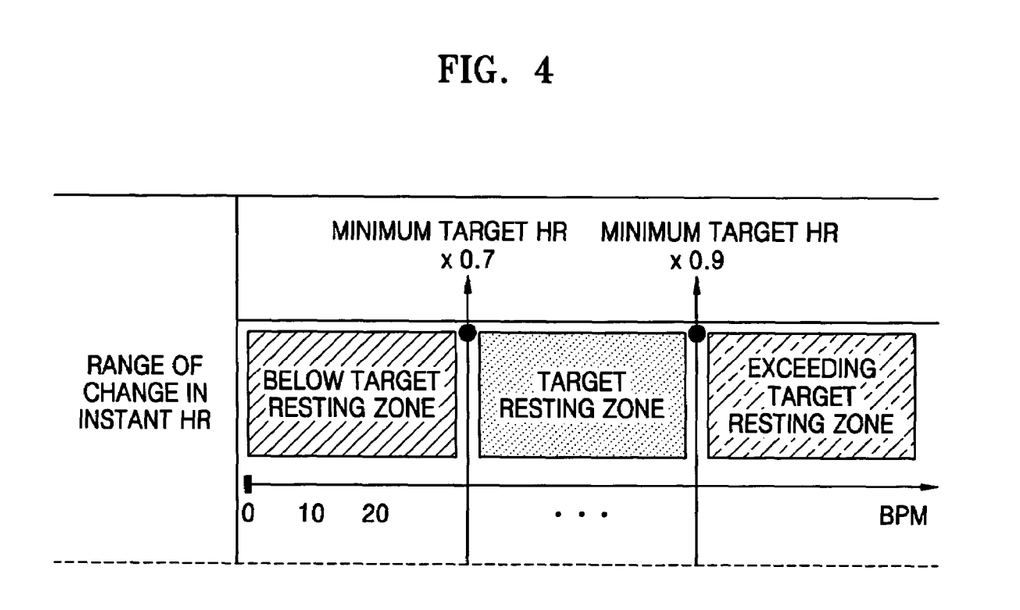
FIG. 4 illustrates a target resting zone and its corresponding biofeedback.

Referring to FIG. 4, a zone below the lower limit of the target resting zone, i.e., below 70% of the minimum target HR, is referred to as a "below target resting zone." A zone exceeding the upper limit of the target resting zone, i.e., exceeding 90% of the minimum target HR, is referred to as an "exceeding target resting zone." In the rest training mode, the second positive biofeedback and the second negative biofeedback may be determined based on the target resting zone in the following two manners.

In the first manner, the second positive biofeedback is used when the current HR with a slight deviation continuously remains within the target resting zone for a predetermined period of time and leads the user to a stable rest in which the user's current HR remains within the target resting zone. To implement the second positive biofeedback, the users hears several music files having rhythm similar to an average HR in the target resting zone, i.e., 80% of the minimum target HR. The second negative biofeedback is used when the current HR with a slight deviation continuously remains within the exceeding target resting zone for a predetermined period of time and encourages the user to relax to spontaneously reach the target resting zone. To implement the second negative biofeedback, the user hears several music files having rhythms gradually progressing from a beat similar to an HR corresponding to the upper limit of the target resting zone to a slower beat similar to an average HR in the target resting zone.

In the second manner, the second positive biofeedback is used when the current HR with a slight deviation continuously remains within the exceeding target resting zone for a predetermined period of time in an initial stage of resting and encourages the user to relax to spontaneously reach the target resting zone. To implement the second positive biofeedback, the user hears several music files having rhythms gradually progressing from a beat similar to an HR corresponding to the upper limit of the target resting zone to a slower beat similar to an average HR in the target resting zone. The second negative biofeedback is used when the current HR increases from the target resting zone to the exceeding target resting zone and informs the user of an ineffectiveness of the rest. To implement the second negative biofeedback, the user hears several music files having rhythm of a faster beat than the average current HR for the predetermined period of time. In addition, when a current HR continuously remains in the target resting zone for a long time or falls below the target resting zone, it is determined that the user is satisfactorily resting, and biofeedback is stopped.

Referring back to FIG. 2, in operation 215, when the user selects either of the exercise training mode or the rest training mode, it is determined whether the current HR remains within a target zone of the selected training mode, i.e., within either of the target exercise zone or the target resting zone, for a predetermined period of time, and it is determined which of the positive biofeedback and the negative biofeedback corresponds to the determined current HR conditions. Here, a current HR is recorded every second and is compared with the lower and the upper limits of the target exercise zone or the target resting zone at predetermined time intervals.

In operation 216, when a result of the comparison determines that the change in the current HR corresponds to the negative biofeedback in the selected training mode, the negative biofeedback is determined and negative biofeedback information is supplied to the user. In operation 217, when the result of the comparison determines that a change in the current HR corresponds to the positive biofeedback in the selected training mode, the positive biofeedback is determined and positive biofeedback information is supplied to the user. The positive biofeedback information and the negative biofeedback information may be subdivided. In this case, a music file in a memory block is subdivided by means of predetermined beat units, for example, five (5) beat units.

Figure 5:
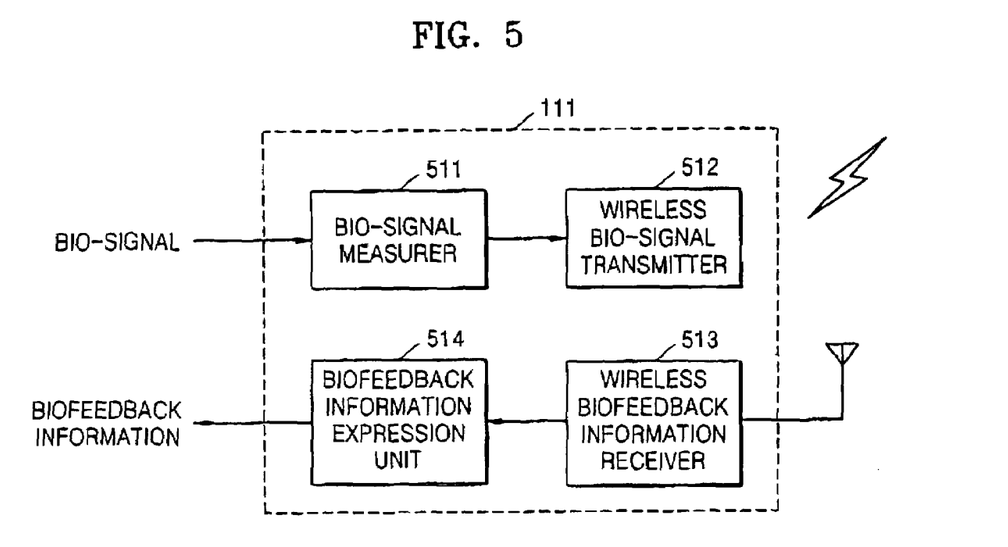
FIG. 5 is a detailed block diagram of a bio-signal measuring module shown in FIG. 1.

FIG. 5 is a detailed block diagram of the bio-signal measuring module 111 shown in FIG. 1. The bio-signal measuring module 111 measures a bio-signal from a user and provides biofeedback information received from the bio-information feedback module 121 to the user. The bio-signal measuring module 111 includes a bio-signal measurer 511 for measuring a bio-signal, e.g., a PPG signal, a wireless bio-signal transmitter 512 for wirelessly transmitting the bio-signal to the bio-information feedback module 121, a wireless biofeedback information receiver 513 for wirelessly receiving biofeedback information from the bio-information feedback module 121, and a biofeedback information expression unit 514 for providing the biofeedback information to the user. Although not shown, a power supply unit for supplying a power needed in the bio-signal measuring module 111 is also provided.

Figure 6:
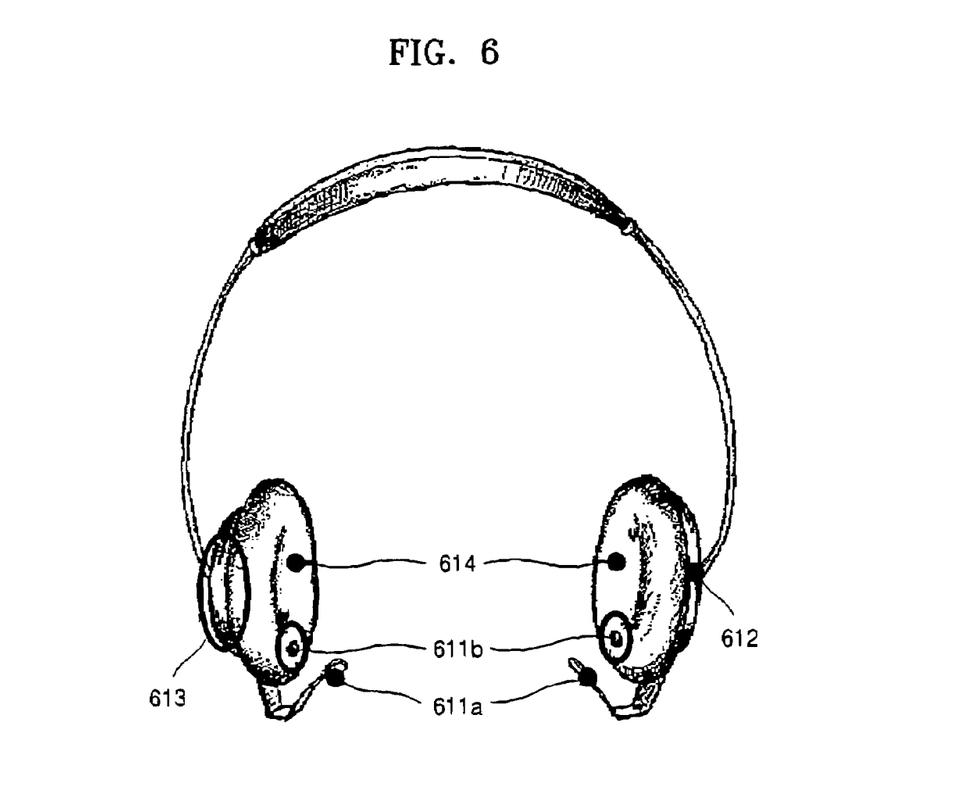
FIG. 6 illustrates an example of the bio-signal measuring module shown in FIG. 1.

FIG. 6 shows an example of the bio-signal measuring module 111 implemented by a headset. Reference numerals 611a and 611b denote a light source and a light receiver, respectively, and correspond to the bio-signal measurer 511. Reference numerals 612 and 613 correspond to the wireless bio-signal transmitter 512 and the wireless biofeedback information receiver 513, respectively. Reference numeral 614 denotes a speaker corresponding to the biofeedback information expression unit 514. In detail, the wireless bio-signal transmitter 612 transmits a PPG signal measured using the light sources 611a and the light receivers 611b to the bio-information feedback module 121. The wireless biofeedback information receiver 613 receives biofeedback information from the bio-information feedback module 121 and outputs it through the speakers 614. The bio-signal measurer 511 including the light sources 611a and the light receivers 611b may be implemented by attaching a transmissive light sensor to an earlobe to minimize an effect of a motion artifact during exercise or rest and to maximize the user's comfort and convenience.

When the bio-signal measuring module 111 is implemented by a headset including a transmissive light sensor, music, i.e., biofeedback information, corresponding to a measured bio-signal such as a PPG signal can be provided to a user through a speaker of the headset. Alternatively, when the bio-signal measuring module 111 is implemented by a headset and a chest band, a respiration rate may be measured using a strain gauge attached to the chest band or body temperature may be measured using a thermocouple, and music that is biofeedback information corresponding to a result of the measurement may be provided to a user through a speaker of the headset. As another alternative, when the bio-signal measuring module 111 is implemented in a shoe and a headset, a variation between a user's weight before exercise and the user's weight after the exercise may be measured using a pressure sensor installed at the shoe or the number of paces may be measured using a photo coupler and a vibration element, and music that is biofeedback information corresponding to the result of the measurement may be provided to the user through a speaker of the headset. Meanwhile, in all of the above-described implementations, in addition to the music, bio-information may be output in the form of a voice signal through the speaker of the headset at predetermined intervals, e.g., at intervals of one (1) minute, during exercise or rest.

Figure 7:
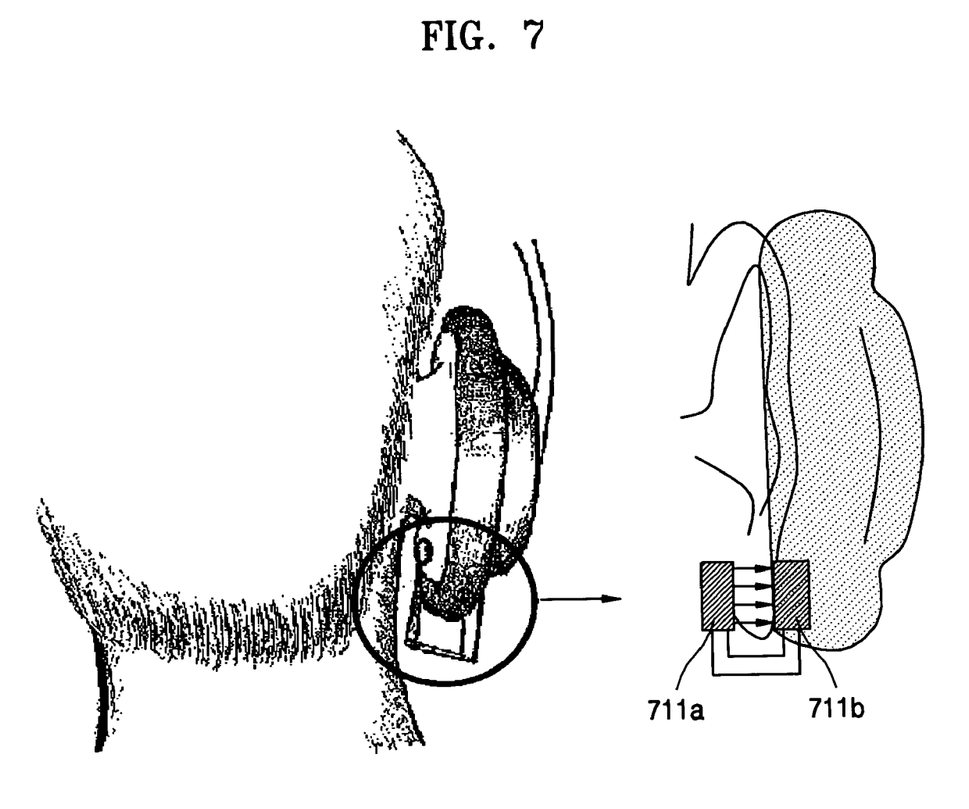
FIG. 7 illustrates an example of a bio-signal measurer shown in FIG. 6.

FIG. 7 illustrates an example of a bio-signal measurer 611a and 611b shown in FIG. 6, in which the bio-signal measurer is implemented by a transmissive light sensor. The transmissive light sensor includes a light source 711a and a light receiver 711b and has a shape of a nipper that can be opened and closed when the transmissive light sensor is attached to the user's earlobe. The transmissive light sensor is illustrated as being installed at a lower portion of a headset.

Figure 8:
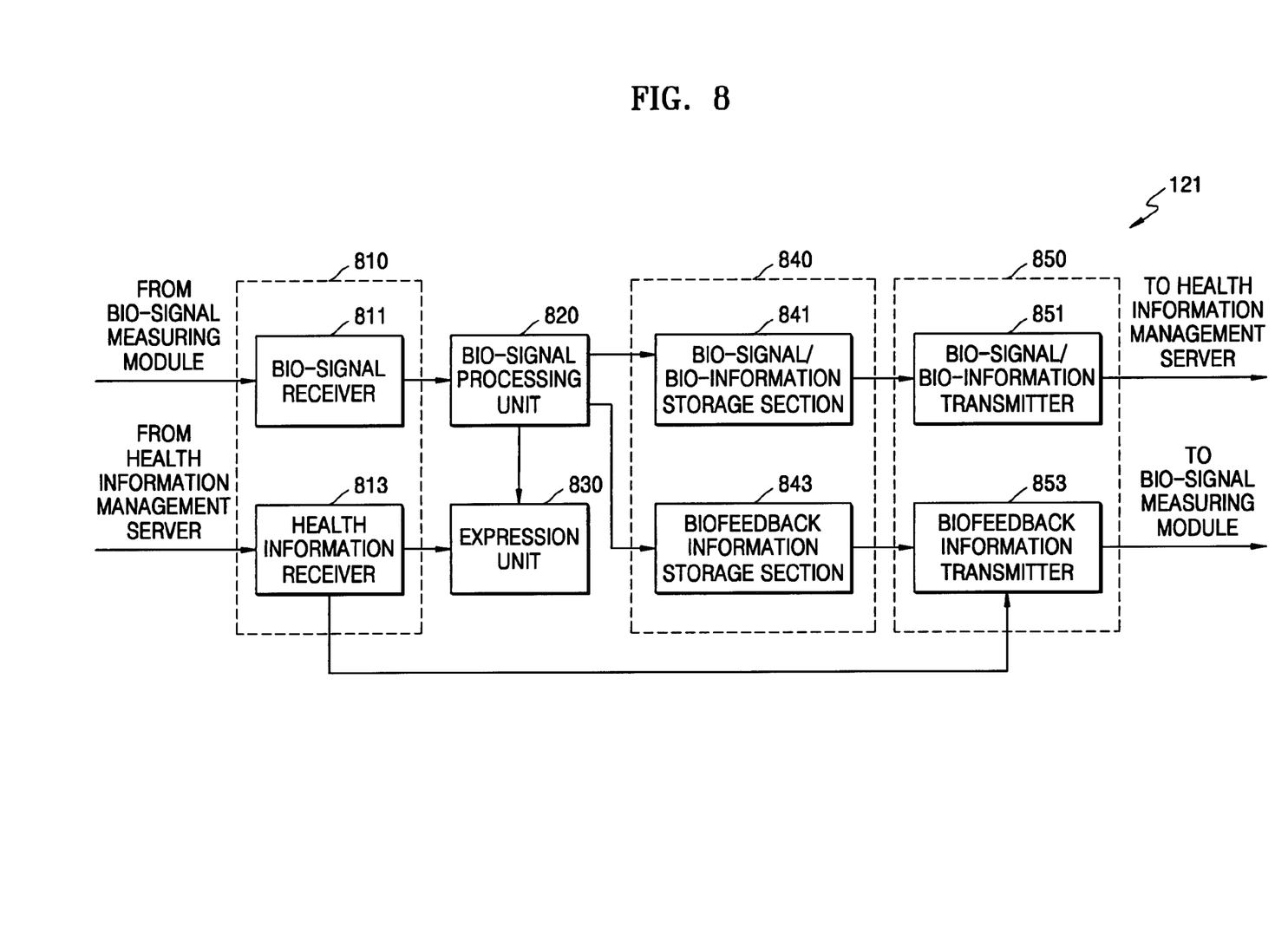
FIG. 8 is a detailed block diagram of a bio-information feedback module shown in FIG. 1.

FIG. 8 is a detailed block diagram of the bio-information feedback module 121 shown in FIG. 1. The bio-information feedback module 121 includes a data receiving unit 810, a bio-signal processing unit 820, an expression unit 830, an information storage unit 840, and an information transmitting unit 850. Like the bio-signal measuring module 111, a power supply unit (not shown) for supplying power needed in the bio-information feedback module 121 is also provided.

Referring to FIG. 8, the data receiving unit 810 includes a bio-signal receiver 811 for receiving a bio-signal, e.g., a PPG, respiration rate, body temperature, body weight variation, or a pace count, from the bio-signal measuring module 111, and a health information receiver 813 for receiving health information from the health information management server 131.

The bio-signal processing unit 820 performs operations necessary to entirely control the bio-information feedback module 121 and particularly performs a series of operations on the bio-signal received from the bio-signal receiver 811 in time units. The bio-signal processing unit 820 selects biofeedback information corresponding to a result of the operations on the bio-signal and stores the selected biofeedback information in a biofeedback information storage section 843 included in the information storage unit 840. The bio-signal processing unit 820 includes a storage medium for storing positive biofeedback information and negative biofeedback information based on the target exercise zone and positive biofeedback information and negative biofeedback information based on the target resting zone. Here, the positive biofeedback information and the negative biofeedback information are divided into a plurality of beat levels and a plurality of music files is included in each of the beat levels. The bio-signal processing unit 820 determines which of the positive biofeedback and the negative biofeedback in a training mode selected by a user corresponds to the result of the operations on the bio-signal and selects, as the biofeedback information, music files having at least one of the beat levels according to the current HR. In addition, the bio-signal processing unit 820 stores a result of the analysis of the bio-signal received from the bio-signal receiver 811, i.e., bio-information such as an HR, a respiratory rate, body temperature, or body weight variation, in a bio-signal/bio-information storage section 841 together with the bio-signal.

The expression unit 830 displays on a screen or outputs in the form of voice or sound the operation result received from the bio-signal processing unit 820 and the health information received from the health information receiver 813. For example, the expression unit 830 may be a liquid crystal display (LCD) unit or a speaker.

The information storage unit 840 includes the bio-signal/bio-information storage section 841 for storing the bio-signal received from the bio-signal measuring module 111 and the bio-information collected by performing operations on the bio-signal, and the biofeedback information storage section 843 for storing the biofeedback information to be transmitted to the bio-signal measuring module 111. Here, the biofeedback information may be an auditory signal, e.g., music or voice, defined according to a result of comparing a current HR with a target HR zone for exercise training or rest training. In addition, the biofeedback information may include bio-information output in the form of a voice signal at predetermined intervals during exercise or rest.

The information transmitting unit 850 includes a bio-signal/bio-information transmitter 851 for transmitting the bio-signal and the bio-information to the health information management server 131 and a biofeedback information transmitter 853 for transmitting the biofeedback information to the bio-signal measuring module 111.

Figure 9:
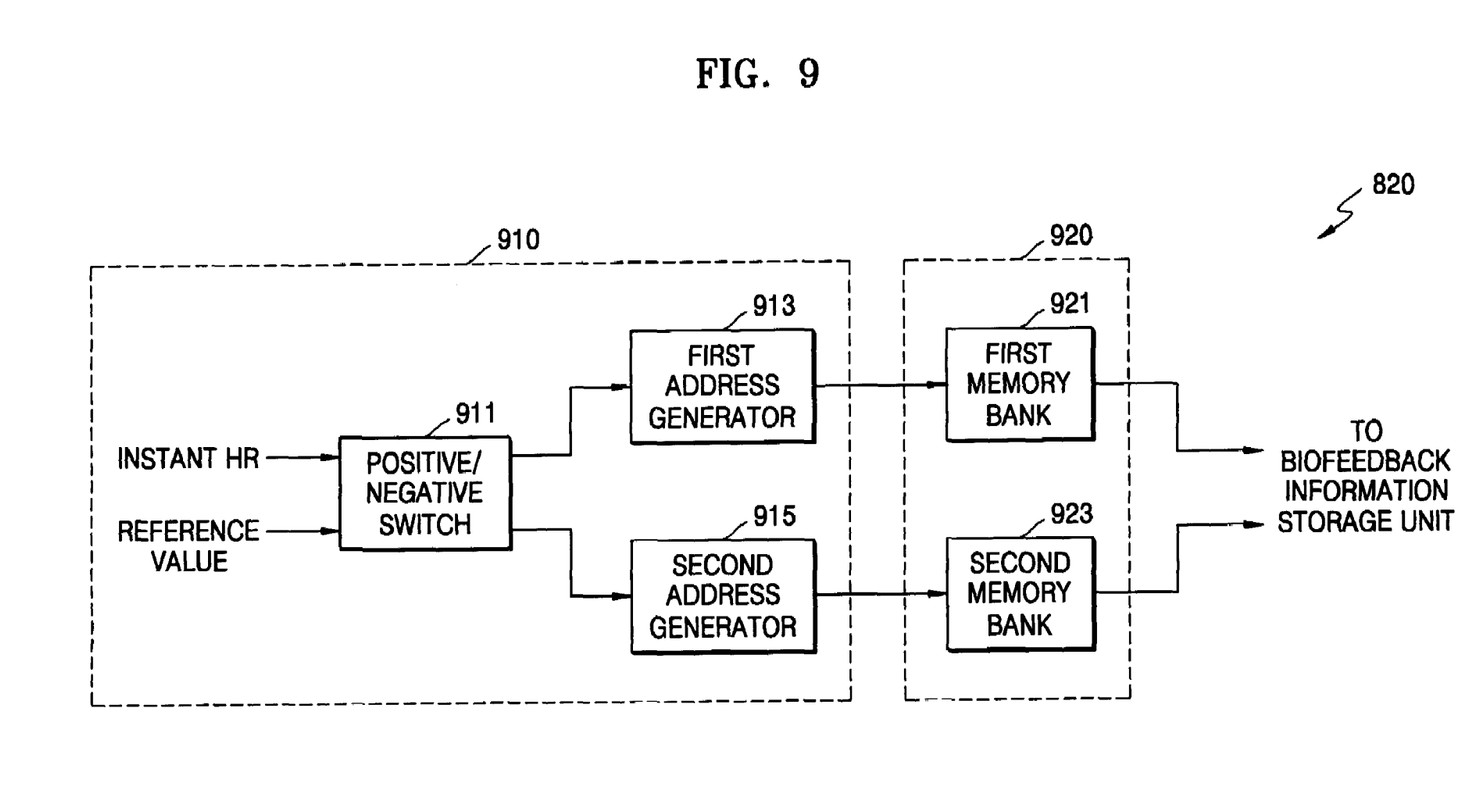
FIG. 9 is a detailed block diagram of a bio-signal processing unit shown in FIG. 8.

FIG. 9 is a detailed block diagram of the bio-signal processing unit 820 shown in FIG. 8. The bio-signal processing unit 820 includes a selection signal generator 910 including a positive/negative switch 911, a first address generator 913, and a second address generator 915; and a biofeedback information generator 920 including a first memory bank 921 and a second memory bank 923. In an alternative embodiment in which the first and second memory banks 921 and 923 are integrated into a single memory bank, the positive/negative switch 911 can be omitted and the first and second address generators 913 and 915 can also be integrated into a single address generator.

Referring to FIG. 9, in the selection signal generator 910, the positive/negative switch 911 sets a reference value, i.e., a target zone, according to a training mode selected by a user and compares the reference value with a current HR in time units. For example, when the exercise training mode is selected by the user, the reference value is set to the target exercise zone. Similarly, when the rest training mode is selected, the reference value is set to the target resting zone. By way of example with reference to the second manner described above, while continuously comparing the user's current HR with the target zone, when the current HR remains out of the target zone for a predetermined period of time, the positive/negative switch 911 determines the positive biofeedback information to be the appropriate biofeedback information and applies an enable signal and beat levels of music files to be the feedback to the first address generator 913 in order to lead the current HR to the target zone. However, when the current HR that has previously been within the target zone remains out of the target zone for a predetermined period of time, the positive/negative switch 911 determines the negative biofeedback information to be the appropriate biofeedback information and applies the enable signal and beat levels of music files to be the feedback to the second address generator 915 in order to inform the user of the deviation from the target zone.

In another embodiment of the present invention, i.e., the first manner as described above, while continuously comparing the user's current HR with the target zone, when the current HR remains within the target zone, the positive/negative switch 911 determines the positive biofeedback information to be the appropriate biofeedback information and applies the enable signal and beat levels of music files to be the feedback to the first address generator 913 in order to maintain the current HR within the target zone. When the current HR remains out of the target zone for a predetermined period of time, the positive/negative switch 911 determines the negative biofeedback information to be the appropriate biofeedback information and applies the enable signal and beat levels of music files to be feedback to a user to the second address generator 915 in order to lead the current HR to the target zone.

The first and second address generators 913 and 915 operate in response to the enable signal and generate address signals, respectively, according to beat levels of music files to be feedback to a user, to select one sector or a plurality of sectors in each of the first and second memory banks. For example, when the first positive biofeedback information is determined to be the appropriate feedback in the exercise training mode in the second manner, memory sectors sequentially storing a music file having a beat similar to the lower limit of the target exercise zone to a music file having a beat similar to an average HR in the target exercise zone are selected by the address signal. When the first negative biofeedback information is determined to be the appropriate feedback in the exercise training mode in the second manner, a memory sector storing music files having a slower beat than the current HR is selected by the address signal. When the second positive biofeedback information is determined to be the appropriate feedback in the rest training mode in the second manner, memory sectors sequentially storing a music file having a beat similar to the upper limit of the target resting zone to a music file having a beat similar to an average HR in the target resting zone are selected by the address signal. When the second negative biofeedback information is determined to be the appropriate feedback in the rest training mode in the second manner, a memory sector storing music files having a faster beat than the current HR is selected by the address signal.

In another embodiment of the present invention, i.e., the first manner, when the first positive biofeedback information is determined to be the appropriate feedback in the exercise training mode, a memory sector storing music files having a beat similar to an average HR in the target exercise zone is selected by the address signal. When the first negative biofeedback information is determined to be the appropriate feedback in the exercise training mode, memory sectors sequentially storing a music file having a beat similar to the lower limit of the target exercise zone to a music file having a beat similar to an average HR in the target exercise zone are selected by the address signal. When the second positive biofeedback information is determined to be the appropriate feedback in the rest training mode, a memory sector storing music files having a beat similar to an average HR in the target resting zone is selected by the address signal. When the second negative biofeedback information is determined to be the appropriate feedback in the rest training mode, memory sectors sequentially storing a music file having a beat similar to the upper limit of the target resting zone to a music file having a beat similar to an average HR in the target resting zone are selected by the address signal.

The first and second memory banks 921 and 923 store the positive biofeedback information and the negative biofeedback information, respectively, and comprise a plurality of memory sectors corresponding to beat levels. In each of the memory sectors, a plurality of digital music files having identical beat levels is included. Addresses generated by each of the first and second address generators 913 and 915 are mapped to the memory sectors in each corresponding one of the first and second memory banks 921 and 923 in advance.

The number of addresses to be generated is one or more according to a type of biofeedback. First, the first manner for determining the first and second positive biofeedback and the first and second negative biofeedback will be described. When it is determined that the first positive biofeedback information is to be supplied to the user in the exercise training mode, an address signal for designating a memory sector storing a music file having a beat similar to an average HR in the target exercise zone is repeatedly generated. Then, a plurality of music files are randomly read from the designated memory sector in the first memory bank 921. When it is determined that the first negative biofeedback information is to be supplied to the user in the exercise training mode, a plurality of address signals for designating memory sectors storing a music file having a beat similar to the lower limit of the target exercise zone to a music file having a beat similar to an average HR in the target exercise zone are sequentially generated. Then, a music file is randomly selected from each of the designated memory sectors in the second memory bank 923 and the selected music files are sequentially read in ascending order of beat.

When it is determined that the second positive biofeedback information is to be supplied to the user in the rest training mode, an address signal for designating a memory sector storing a music file having a beat similar to an average HR in the target resting zone is repeatedly generated. Then, a plurality of music files are randomly read from the designated memory sector in the first memory bank 921. When it is determined that the second negative biofeedback information is to be supplied to the user in the rest training mode, a plurality of address signals for designating memory sectors storing a music file having a beat similar to the upper limit of the target resting zone to a music file having a beat similar to an average HR in the target resting zone are sequentially generated. Then, a music file is randomly selected from each of the designated memory sectors in the second memory bank 923 and the selected music files are sequentially read in descending order of beat.

Second, the second manner for determining the first and second positive biofeedback and the first and second negative biofeedback is now described. When it is determined that the first positive biofeedback information is to be supplied to the user in the exercise training mode, a plurality of address signals for designating memory sectors storing a music file having a beat similar to the lower limit of the target exercise zone to a music file having a beat similar to an average HR in the target exercise zone are sequentially generated. Then, a music file is randomly selected from each of the designated memory sectors in the first memory bank 921 and the selected music files are sequentially read from in ascending order of beat. When it is determined that the first negative biofeedback information is to be supplied to the user in the exercise training mode, an address signal for designating a memory sector storing a music file having a slower beat than a current HR is repeatedly generated. Then, a plurality of music files are randomly read from the designated memory sector in the second memory bank 923.

When it is determined that the second positive biofeedback information is to be supplied to the user in the rest training mode, a plurality of address signals for designating memory sectors storing a music file having a beat similar to the upper limit of the target resting zone to a music file having a beat similar to an average HR in the target resting zone are sequentially generated. Then, a music file is randomly selected from each of the designated memory sectors in the first memory bank 921 and the selected music files are sequentially read in descending order of beat. When it is determined that the second negative biofeedback information is to be supplied to the user in the rest training mode, an address signal for designating a memory sector storing a music file having a faster beat than a current HR is repeatedly generated. Then, a plurality of music files are randomly read from the designated memory sector in the second memory bank 923.

Determination of the positive biofeedback and the negative biofeedback in each training mode may be performed using other various methods than those described in the above-described embodiments. According to the methods of determining the positive biofeedback and the negative biofeedback, beat levels of music files provided as the positive or negative biofeedback information may be configured in various ways to lead a user's current HR to the target exercise zone or the target resting zone.

The invention can also be embodied as computer readable codes on a computer readable recording medium. The computer readable recording medium is any data storage device that can store data that can be thereafter read by a computer system. Examples of the computer readable recording medium include read-only memory (ROM), random-access memory (RAM), CD-ROMs, magnetic tapes, floppy disks, optical data storage devices, and carrier waves (such as data transmission through the Internet). The computer readable recording medium can also be distributed over network coupled computer systems so that the computer readable code is stored and executed in a distributed fashion. In addition, functional programs, codes, and code segments for accomplishing the present invention can be easily construed by programmers skilled in the art to which the present invention pertains.

As described above, according to the present invention, when a user's current HR is lower than a lower limit of a target exercise zone during exercise, music having beats faster than the user's current HR are provided to the user so that the user can exercise to the music having the faster beats. As a result, the user is spontaneously motivated to exercise more vigorously, thereby increasing the user's HR. On the other hand, when the user's current HR is higher than an upper limit of a target resting zone during a rest, music having beats slower than the user's current HR are provided to the user. Since the user continuously hears the music having the beats slower than the current HR, the user can be spontaneously encouraged to relax, thereby decreasing the user's HR, which results in a more stable resting state.

In addition, according to the present invention, a bio-signal measuring module has a structure in which a transmissive light sensor that includes a light source and a light receiver and has a shape of a nipper that can be opened and closed when the transmissive light sensor is attached to the user's earlobe is installed at a lower portion of a headset so that PPG can be measured. Accordingly, a contact between the transmissive light sensor and the user's earlobe can be reliably maintained even while the user is exercising. As a result, a bio-signal can be measured with a high signal-to-noise ratio (SNR) even when a motion artifact occurs.

Moreover, since health information is managed by different conditions, such as users and periods based on bio-information obtained from a bio-signal measured from a user, and is fed back to the user, the present invention can contribute to promoting the user's health.

Exemplary embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A training control apparatus using biofeedback, comprising:

a bio-signal measuring module for measuring a bio-signal from a user and for providing predetermined biofeedback information to the user; and a bio-information feedback module for setting a target exercise zone and a target resting zone using the bio-signal received from the bio-signal measuring module and user information, for comparing the bio-signal with the target exercise zone and the target resting zone according to a preselected training mode, and for providing one of a positive biofeedback information and a negative biofeedback information to the bio-signal measuring module according to a result of the comparison, wherein the bio-information feedback module provides a plurality of music files having an identical beat or a plurality of music files having different beats to the user as the positive or negative biofeedback information according to a current heart rate obtained from the bio-signal in an exercise training mode to lead the current heart rate to the target exercise zone or to inform the user of a deviation from the target exercise zone, wherein the bio-information feedback module provides a plurality of music files having an identical beat or a plurality of music files having different beats to the user as the positive or negative biofeedback information according to a current heart rate obtained from the bio-signal in an resting training mode to lead the current heart rate to the target resting zone or to inform the user of a deviation from the target resting zone.

2. The training control apparatus as claimed in claim 1, wherein the bio-information feedback module includes a memory for storing a plurality of music files having different beats.

3. The training control apparatus as claimed in claim 1, wherein the bio-signal measuring module is a headset including a speaker, a transmissive light sensor, and a wireless transceiver.

4. The training control apparatus as claimed in claim 1, wherein the bio-information feedback module is one selected from the group consisting of a mobile communication terminal, a personal digital assistant (PDA) capable of wireless data communication, and a wristwatch-type information terminal.

5. The training control apparatus as claimed in claim 1 further comprising a health information management server for receiving the bio-signal and
bio-information from the bio-information feedback module, for periodically managing a result of analyzing the bio-signal and the bio-information as health information of the user, and for transmitting the periodic health information to the bio-information feedback module so that the periodic health information is provided to the user.

6. The training control apparatus as claimed in claim 5, wherein the health information management server is installed at either of a data center and a base station.

7. The training control apparatus as claimed in claim 1, wherein the bio-information feedback module provides a warning message to the user according to the result of the comparison.

8. The training control apparatus as claimed in claim 1, wherein the bio-information feedback module calculates a maximum target heart rate using an initial heart rate of the user and user information, and uses the maximum target heart rate to set the target exercise zone.

9. The training control apparatus as claimed in claim 1, wherein the bio-information feedback module calculates a minimum target heart rate using an initial heart rate of the user and user information, and uses the minimum target heart rate to set the target resting zone.

10. The training control apparatus as claimed in claim 1, wherein the bio-information feedback module provides the positive biofeedback information
including a plurality of music files having a beat similar to an average heart rate in the target exercise zone, and the negative biofeedback information including a plurality of music files having a beat similar to the lower limit of the target exercise zone through a beat similar to the average heart rate in the target exercise zone.

11. The training control apparatus as claimed in claim 1, wherein the bio-information feedback module provides the positive biofeedback information including a plurality of music files having a beat similar to the lower limit of the target exercise zone through a beat similar to the average heart rate in the target exercise zone, and the negative biofeedback information including a plurality of music files having a slower beat than the current heart rate.

12. The training control apparatus as claimed in claim 1, wherein the bio-information feedback module provides the positive biofeedback information including a plurality of music files having a beat similar to an average heart rate in the target resting zone, and the negative biofeedback information including a plurality of music files having a beat similar to the upper limit of the target resting zone through a beat similar to the average heart rate in the target resting zone.

13. The training control apparatus as claimed in claim 1, wherein the bio-information feedback module provides wherein the positive biofeedback information including a plurality of music files having a beat similar to the upper limit of the target resting zone through a beat similar to an average heart rate in the target resting zone, and the negative biofeedback information including a plurality of music files having a faster beat than the current heart rate.

14. The training control apparatus as claimed in claim 1, wherein the bio-information feedback module compares a current heart rate of the user with the target exercise zone, provides the positive biofeedback information to the user to maintain the current heart rate within the target exercise zone, when the current heart rate remains within the target exercise zone for longer than a first time, provides the negative biofeedback information to the user to increase the current heart rate to the target exercise zone, when the current heart rate remains below the target exercise zone for longer than a second time, and provides a warning message to the user, when the current heart rate is greater than the target exercise zone.

15. The training control apparatus as claimed in claim 1, wherein the bio-information feedback module compares a current heart rate of the user with the target resting zone, provides the positive biofeedback information to the user, when the current heart rate remains within the target resting zone for longer than a first time, provides the negative biofeedback information to the user, when the current heart rate remains above the target resting zone for longer than a second time, and stops biofeedback, the current heart rate remains within the target resting zone for longer than a third time or is less than the target resting zone.

* * * * *